United States Patent [19]

Kleiner

[11] Patent Number: 4,632,995
[45] Date of Patent: Dec. 30, 1986

[54] PROCESS FOR THE PREPARATION OF PHENYL- AND THIENYL-CHLOROPHOSPHANE DERIVATIVES

[75] Inventor: Hans-Jerg Kleiner, Kronberg, Fed. Rep. of Germany

[73] Assignee: Hoechst Aktiengesellschaft, Frankfurt am Main, Fed. Rep. of Germany

[21] Appl. No.: 599,539

[22] Filed: Apr. 12, 1984

[30] Foreign Application Priority Data

Apr. 16, 1983 [DE] Fed. Rep. of Germany ....... 3313921

[51] Int. Cl.$^4$ .................. C07D 333/30; C07F 9/42
[52] U.S. Cl. ........................ 549/6; 568/14; 568/16; 568/17
[58] Field of Search .............. 549/6, 216; 568/14, 568/16, 17

[56] References Cited

U.S. PATENT DOCUMENTS 3,972,923 11/1973 Finke et al. ................ 260/543

FOREIGN PATENT DOCUMENTS 362026 12/1972 U.S.S.R. .................. 568/14

OTHER PUBLICATIONS

Houben-Weyl, *Methoden Der Organischen Chemie*, vol. XII/I (1963), p. 140.
English Abstract of the Kharrasova et al., reference (USSR 362026).
Angew. Chemie—Intern. edition in English—vol. 20, No. 3, Mar. 1981, pp. 223–233.
Chem. Ber. 103, pp. 2428–2436 (1970).
C.A. vol. 98 (1983), p. 205.
Eurp. Search Report.
Bull. of Academy of Sciences USSR vol. 28 (1979), pp. 394–399.

*Primary Examiner*—Henry R. Jiles
*Assistant Examiner*—J. G. Mullins
*Attorney, Agent, or Firm*—Curtis, Morris & Safford

[57] ABSTRACT

Organic chlorophosphanes of the formula II

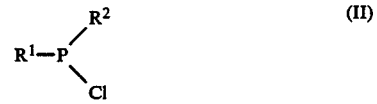

(II)

in which $R^1$=an aromatic or heterocyclic radical and $R^2$=an aliphatic radical or Cl are prepared by reacting organic phosphorus oxychlorides of the formula I

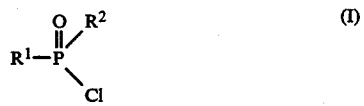

(I)

in which $R^1$ and $R^2$ have the meaning mentioned above with triphenylphosphane $(C_6H_5)_3P$ at an elevated temperature. The organic chlorophosphanes II are, in the main, intermediates in various specialized fields, such as the pharmaceuticals, plant protection, dyestuffs and polymers sectors.

4 Claims, No Drawings

PROCESS FOR THE PREPARATION OF PHENYL- AND THIENYL-CHLOROPHOSPHANE DERIVATIVES

Organic chlorophosphanes are compounds of the general formulae

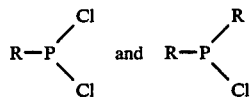

wherein R = an organic radical.

They are, in the main, intermediates in various specialized fields, such as the pharmaceuticals, plant protection, dyestuffs and polymer sectors.

A number of different methods are known for their preparation. In particular, aliphatic chlorophosphanes—especially methyldichlorophosphane—can, for example, be prepared by the method described in Soviet Union Inventor's Certificate No. 362,026; this method comprises the reaction (deoxygenation) of methylphosphonic acid dichloride with an aliphatic phosphane—tri-n-butylphosphane (n—$C_4H_9$)$_3$P and tri-i-amylphosphane (i—$C_5H_{11}$)$_3$P are mentioned in particular—in a molar ratio of 1:1 at temperatures between 175° and 220° C. The reaction is based on the following equation:

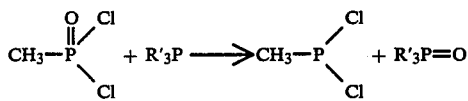

methylphosphonic acid dichloride / methyldi-chlorophosphane / trialkyl-phosphane / trialkyl-phosphane oxide
(R' = an aliphatic radical)

The yields of methyldichlorophosphane reported are about 60% of theory; for the trialkylphosphane oxide, the yields are between about 80 and 90% of theory.

If the aliphatic phosphane is replaced in this reaction of triphenylphosphane ($C_6H_5$)$_3$P, which is more readily accessible from a technical point of view and cheaper, the yield of alkyldichlorophosphane obtained is—as our experiments have shown—inadequate for practical requirements (less than 30% of theory). In the attempt to develop further the reaction according to the above-mentioned Soviet Union Inventor's Certificate and, in particular, to modify it in such a way that it also takes place at usable yields with triphenylphosphane (instead of the aliphatic phosphanes), it has now been found that this aim can be achieved by employing aromatic or heterocyclic phosphonic acid dichlorides instead of the aliphatic (in the known reaction) phosphonic acid dichloride; the use of aromatic-aliphatic or heterocyclic-aliphatic phosphinic acid chlorides is also possible.

The invention relates, therefore, to a process for the preparation of organic chlorophosphanes by reacting organic phosphorous oxychlorides with an organic phosphane at an elevated temperature, which comprises using, as organic phosphorus oxychlorides, compounds of the formula I

in which $R^1$ = an aromatic or heterocyclic radical and $R^2$ = an aliphatic radical or Cl, and, as the organic phosphane, triphenylphosphane ($C_6H_5$)$_3$P.

This reaction enables aromatic and heterocyclic dichlorophosphanes and also aromatic-aliphatic and heterocyclic-aliphatic monochlorophosphanes—the dichlorophosphanes and monochlorophosphanes are labeled II here—to be obtained in high yields (in most cases between about 75 and 100% of theory) in accordance with the equation

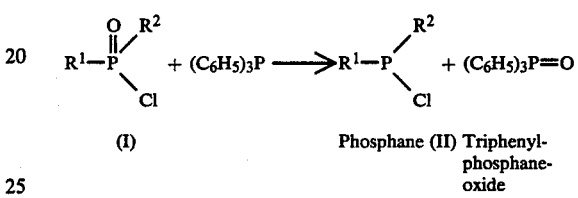

(I)  Phosphane (II)  Triphenyl-phosphane-oxide

The success and the smooth course of this reaction were extremely surprising, because only relatively little dichlorophosphane is formed in the reaction of purely aliphatic phosphonic acid dichlorides with triphenylphosphane.

The starting materials for the process according to the invention are the compounds of the formula I and triphenylphosphane.

In formula I, the aromatic or heterocyclic radical $R^1$ is preferably the phenyl or thienyl radical—if appropriate substituted by inert groups. Inert groups are groups which do not react in the reaction which takes place here. Preferred inert groups of this type are in this case alkyl groups, halogenoalkyl groups and halogen groups, in particular $C_1$-$C_6$-alkyl groups (above all $CH_3$ and $C_2H_5$), $CF_3$ and Cl. Both the phenyl and the thienyl radical can be monosubstituted or polysubstituted; preferably, the phenyl radical is monosubstituted or disubstituted and the thienyl radical is unsubstituted.

If $R^2$ = an alkyl radical, a $C_1$-$C_6$-alkyl radical is preferred; the $CH_3$ radical and the $C_2H_5$ radical are particularly preferred.

Of the two possibilities for $R^2$ (alkyl radical or Cl), Cl is preferred.

If $R^2$ = an alkyl radical, the compounds of the formula I are aromatic-aliphatic or heterocyclic-aliphatic phosphinic acid chlorides, such as, for example, phenylmethylphosphinic acid chloride, tolylmethylphosphinic acid chloride, phenylethylphosphinic acid chloride or thienylmethylphosphinic acid chloride etc. The compounds are accessible by known methods.

If $R^2$ = Cl in formula I, the compounds are aromatic and heterocyclic phosphonic acid dichlorides, such as, for example, phenylphosphonic acid dichloride, tolylphosphonic acid dichlorides, xylylphosphonic acid dichlorides, 3-trifluoromethylphenylphosphonic acid dichloride, 4-chlorophenylphosphonic acid dichloride, thienylphosphonic acid dichloride etc. The preparation of these compounds also is effected by known methods. Thus, for example, phenylphosphonic acid dichloride $C_6H_5P(O)Cl_2$ is obtainable, inter alia, by phosgenating phenylphosphonic acid diesters ($C_6H_5P(O)(OR)_2$ in which R=an organic radical; phenylphosphonic acid diesters for their part are accessible, for example, by reacting bromobenzene with trialkyl phosphites in the presence of nickel bromide.

The organic phosphorus oxychlorides of the formula I and triphenylphosphane are normally employed in the (stoichiometric) molar ratio of 1:1. Other molar ratios are, however, also possible. Either the phosphorus oxychloride I or the triphenylphosphane can be employed in excess; the excess then remains unreacted in the reaction. In particular, excess organic phosphorus oxychloride I is also suitable as a solvent and diluent for the reaction and in the course of working up. The additional presence of other inert solvents and diluents in possible, but brings no advantages.

In general, the reaction temperature is between about 100° and about 350° C., preferably between about 170° and about 250° C.

Normally, the reaction is carried out under atmospheric pressure; the use of excess pressures is also possible, however, and can be advisable in certain cases.

The reaction is carried out by mixing the organic phosphorus oxychlorides of the formula I with triphenylphosphane in an appropriate manner and keeping the mixture at the reaction temperature for a certain time, preferably under an inert gas atmosphere (for example nitrogen); the duration of the reaction is, on average, about 1 to 20 hours.

When the reaction is complete, the chlorophosphane II—i.e. monochlorophosphane (from phosphinic acid chloride I) or dichlorophosphane (from phosphonic acid dichloride I)—has to be isolated. Triphenylphosphane oxide is formed as a second reaction product. Isolation can, for example, be carried out by distillation, for example also with the aid of a thin film evaporator adjusted so that the low-boiling chlorophosphanes II and, if appropriate, also the organic phosphorus oxychlorides I distil off, while the triphenylphosphane oxide and, if appropriate, the triphenylphosphane pass into the still bottom. Sometimes the bulk of the triphenylphosphane oxide formed also crystallizes out from the reaction mixture; a preliminary separation is then possible by means of filtration, if appropriate also in the presence of a diluent.

The process according to the invention makes it possible to obtain chlorophosphanes having an aromatic or heterocyclic radical attached to the phosphorus from organic phosphorus oxychlorides with the concomitant use of triphenylphosphane (which is more readily accessible and cheaper than the purely aliphatic phosphanes according to Soviet Union Inventor's Certificate No. 362,026), in consistently higher yields (compared with the process of the said Soviet Union Inventor's Certificate). The invention therefore constitutes an improved further developement of the process according to Soviet Union Inventor's Certificate No. 362,062.

The examples which follow are intended to illustrate the invention further. The examples of the invention (A) are followed by a comparison example (B) which shows that only relatively little dichlorophosphane is formed in the reaction of purely aliphatic phosphonic acid dichlorides with triphenylphosphane.

A. EXAMPLES OF THE INVENTION

Example 1

50 g (0.256 mole) of phenylphosphonic acid dichloride and 40 g (0.153 mole) of triphenylphosphane were stirred for 12 hours at 230° C. under an atomosphere of nitrogen. Distillation was then carried out at 0.1 kPa until an internal temperature of 200° C. was reached. The distillate obtained was then fractionated using a silvered-jacketed column, 70 cm long, packed with Raschig rings. 25 g of dichlorophenylphosphane were obtained, as well as unreacted phenylphosphonic acid dichloride. This corresponds to a yield of 91% of theory, based on triphenylphosphane employed.

EXAMPLE 2

80 g (0.380 mole) of p-tolylphosphonic acid dichloride and 32 g (0.123 mole) of triphenylphosphane were stirred for 8 hours at 200° C. under an atmosphere of nitrogen. Distillation was then carried out until a top temperature of 140° C. at 0.026 kPa was reached. This gave 70 g of a distillate containing 33.5% of dichloro-p-tolylphosphane (according to $^{31}$P-NMR spectrum) as well as unreacted p-tolyphosphonic acid dichloride. This corresponds to a yield of 99% of theory, based on triphenylphosphane employed.

EXAMPLE 3

317 g (1.52 moles) of o-tolylphosphonic acid dichloride and 400 g (1.53 moles) of triphenylphosphane were stirred for 17 hours at 180° C. under an atmosphere of nitrogen. The mixture was then cooled and the triphenylphosphane oxide which had crystallized out was filtered off with suction. The filtrate was distilled at 0.093 kPa at a top temperature of approx. 80°–100° C. This gave 220 g, containing 45% of dichloro-o-tolylphosphane and 45% of o-tolylphosphonic acid dichloride (according to $^{31}$P-NMR spectrum). The dichloro-o-tolylphosphane was obtained at a yield of 50% of theory, at a 68.5% conversion of o-tolylphosphonic acid dichloride.

It was possible to obtain further quantities of o-tolylphosphonic acid dichloride and dichloro-o-tolylphosphane by special purification from the triphenylphosphane oxide which had crystallized out and had been filtered off with suction.

The distillate was fractionated using a 70 cm silvered-jacketed column, packed with Raschig rings. 90 g of dichloro-o-tolylphosphane were obtained, boiling point: 74° C./0.2 kPa.

EXAMPLE 4

133 g (1.0 mole) of m-xylylphosphonic acid dichloride (2,4-dimethylphenylphosphonic acid dichloride) and 274 g (1.05 moles) of triphenylphosphane were stirred for 12 hours at 220° C. under an atmosphere of nitrogen. The hot reaction mixture was then added dropwise, with stirring, to 600 ml of toluene at room temperature, the triphenylphosphane oxide which had crystallized out was filtered off with suction after 2 hours and was rinsed with ice-cold toluene. The filtrate was freed from toluene under a waterpump vacuum and was then distilled until an internal temperature of 190° C. at approx. 0.175 kPa was reached. This gave 200 g, containing 63% of dichloro-m-xylylphosphane and 25% of m-xylylphosphonic acid dichloride (according to $^{31}$P-NMR spectrum). The yield was about 75% of theory, at a conversion of 79%. The distillate was fractionated using a 70 cm silvered-jacketed column, packed with Raschig rings. This gave pure dichloro-m-xylylphosphane, boiling point: 85° C. 0.093 kPa.

EXAMPLE 5

121 g (0.52 mole) of 3,4-dimethylphenylphosphonic acid dichloride and 283 g (1.08 moles) of triphenylphosphane were stirred for 11 hours at 200° C. under an atmosphere of nitrogen. Distillation was then carried out until an internal temperature of 170° C. at 0.067 kPa was reached. This gave 120 g, containing 45% of dichloro-3,4dimethylphenylphosphane and 48% of 3,4-dimethylphenylphosphonic acid dichloride. This corresponds to a yield of approx. 92% of theory at a conversion of 52.2%. Fractional distillation of the crude distillate gave pure dichloro-3,4-dimethylphenylphosphane, boiling point: 107° C./0.44 kPa.

Dichloro-2,3-dimethylphenylphosphane, boiling point: 87° C./0.0133 kPa, was prepared analogously.

EXAMPLE 6

263 g (1.0 mole) of 3-trifluoromethylphenylphosphonic acid dichloride and 160 g (0.612 mole) of triphenylphosphane were kept at 200° C. for 7 hours under an atmosphere of nitrogen. Distillation was then carried out at 0.4–0.67 kPa until an internal temperature of 190° C. was reached. This gave 245 g, containing 61.5% of dichloro-3,4-trifluoromethylphenylphosphane (according to $^{31}$P-NMR spectrum). This corresponds to a yield of about 100%, based on triphenylphosphane employed. The distillate was fractionated using a 70 cm silvered-jacketed column, packed with Raschig rings. Dichloro-3-trifluoromethylphenylphosphane, boiling point: 78° C./0.8 kPa, was separated from the starting material by this means.

EXAMPLE 7

288 g (1.43 moles) of 2-thienylphosphonic acid dichloride and 375 g (1.43 moles) of triphenylphosphane were stirred for 15 hours at 200° C. under an atmosphere of nitrogen. The hot reaction mixture was then distilled through a thin film evaporator at 200° C. and approx. 0.133 kPa. This gave approx. 200 g of distillate, composed of dichloro-(2-thienyl)-phosphane as well as approx. 5% of bis-(2-thienyl)-chlorophosphane and small quantities of 2-thienylphosphonic acid dichloride. The yield was about 75% of theory. Pure dichloro-(2-thienyl)-phosphane, boiling point: 48° C./0.027 kPa, was obtained by fractionation.

EXAMPLE 8

25 g (0.128 mole) of phenylphosphonic acid dichloride and 30 g (0.115 mol) of triphenylphosphane were kept at 330° C. for 3 hours in a bomb tube. This gave 55 g, containing, on the basis of the $^{31}$P-NMR spectrum, 16.5 g of dichlorophenylphosphane and approx. 4 g of phenylphosphonic acid dichloride as well as triphenylphosphane oxide and a little triphenylphosphane. On the basis of the triphenylphosphane employed, the yield was 86% of theory at a 93% conversion of phenylphosphonic acid dichloride.

EXAMPLE 9

116 g (0.615 mole) of methyl-p-tolyphosphinic acid chloride and 161.5 g (0.617 mole) of triphenylphosphane were stirred for 18 hours at 200° C. under an atmosphere of nitrogen. Distillation was then carried out at 0.53 kPa. 27 g of chloromethyl-p-tolylphosphane were obtained at a top temperature of 90° C. and 0.067 kPa, while 80 g of methyl-p-tolylphosphinic acid chloride were obtained at a top temperature of approx. 120° C. The yield was 82% of theory at a conversion of 25% of theory.

EXAMPLE 10

167 g (0.73 mole) of p-chlorophenylphosphonic acid dichloride and 121 g (0.46 mole) of triphenylphosphane were stirred for 2 hours at 180° C. and for 10 hours at 200° C. under an atmosphere of nitrogen. Distillation was then carried out at 0.04 kPa until a top temperature of 140° C. was reached. This gave 145 g, containing 58.5% of p-chlorophenyldichlorophosphane and 41.5% of p-chlorophenylphosphonic acid dichloride (according to $^{31}$P-NMR spectrum). The distillate was fractionated using a 70 cm silvered-jacketed column, packed with Raschig rings. Pure p-chlorophenyldichlorophosphane (boiling point: 71° C./0.093 kPa) was obtained. This corresponds to a yield of 85% of theory, based on triphenylphosphane employed.

B. COMPARISON EXAMPLE 67.2 g (0.46 mole) of ethanephosphonic acid dichloride and 60 g (0.23 mole) of triphenylphosphane were stirred under a gentle reflux at 195° C. under an atmosphere of nitrogen. In the course of 22 hours, the internal temperature under reflux conditions fell to 185° C. After cooling, distillation was carried out at 5.07 kPa. In the distillation, approx. 8 g of dichloroethylphosphane, which condensed in a cooled receiver, were obtained at a top temperature of 26° C., and 37 g of ethanephosphonic acid dichloride were then obtained at a top temperature of 80° C. up to an internal temperature of 200° C. The residue from the distillation was then distilled at 0.1 kPa. This gave approx. 45 g of unreacted triphenylphosphane.

The yield of dichloroethylphosphane is approx. 27% of theory, based on the triphenylphosphane employed.

I claim:

1. A process for the preparation of an organic chlorophosphane, which comprises reacting an organic phosphorus oxychloride with an organic phosphane at an elevated temperature, wherein the organic phosphorus oxychloride is a compound of the formula I

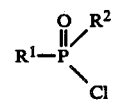

in which $R^1$ is phenyl, phenyl substituted by 1 or 2 alkyl or halo groups or by the $CF_3$ group, or a thienyl group, and $R^2$ is an aliphatic radical or Cl, and triphenylphosphane is the organic phosphane.

2. The process as claimed in claim 1, wherein, in the compounds of the formula I, $R^2$ is a $C_1$–$C_6$-alkyl radical or Cl.

3. The process as claimed in claim 1 or 2, wherein the reaction is carried out at a temperature between about 100 and about 350° C.

4. The process as claimed in claim 3, wherein the reaction is carried out at a temperature between about 170° and 250° C.

* * * * *